(12) United States Patent
Coughlin et al.

(10) Patent No.: US 9,790,237 B2
(45) Date of Patent: Oct. 17, 2017

(54) PROCESSES FOR MAKING ALKYLATED ARYLPIPERAZINE AND ALKYLATED ARYLPIPERIDINE COMPOUNDS INCLUDING NOVEL INTERMEDIATES

(71) Applicant: Johnson Matthey Public Limited Company, London (GB)

(72) Inventors: Daniel J. Coughlin, Mullica Hill, NJ (US); Jeremy C. Wilt, Marlborough, MA (US); Da-Ming Gou, Burlington, MA (US); Steven Collier, Devens, MA (US)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 14/737,599

(22) Filed: Jun. 12, 2015

(65) Prior Publication Data
US 2015/0361099 A1    Dec. 17, 2015

Related U.S. Application Data

(60) Provisional application No. 62/012,701, filed on Jun. 16, 2014.

(51) Int. Cl.

| | | |
|---|---|---|
| C07D 417/12 | (2006.01) |
| C07D 209/56 | (2006.01) |
| C07D 215/227 | (2006.01) |
| C07D 261/20 | (2006.01) |
| C07D 401/12 | (2006.01) |
| C07D 403/12 | (2006.01) |
| C07D 413/12 | (2006.01) |
| C07D 519/00 | (2006.01) |
| C07D 417/08 | (2006.01) |
| C07D 275/06 | (2006.01) |
| C07D 311/20 | (2006.01) |
| C07D 311/06 | (2006.01) |
| C07D 215/22 | (2006.01) |
| C07D 413/04 | (2006.01) |
| C07D 239/88 | (2006.01) |
| C07D 241/04 | (2006.01) |
| C07D 471/12 | (2006.01) |
| C07D 487/12 | (2006.01) |
| C07D 209/52 | (2006.01) |
| C07C 39/00 | (2006.01) |

(Continued)

(52) U.S. Cl.
CPC ............ *C07D 519/00* (2013.01); *C07C 39/00* (2013.01); *C07D 209/52* (2013.01); *C07D 209/56* (2013.01); *C07D 215/22* (2013.01); *C07D 215/227* (2013.01); *C07D 239/88* (2013.01); *C07D 241/04* (2013.01); *C07D 261/20* (2013.01); *C07D 275/06* (2013.01); *C07D 311/06* (2013.01); *C07D 311/20* (2013.01); *C07D 401/12* (2013.01); *C07D 403/12* (2013.01); *C07D 413/04* (2013.01); *C07D 413/12* (2013.01); *C07D 417/08* (2013.01); *C07D 417/12* (2013.01); *C07D 471/12* (2013.01); *C07D 487/12* (2013.01)

(58) Field of Classification Search
None
See application file for complete search history.

(56) References Cited

U.S. PATENT DOCUMENTS

| 5,153,206 A | 10/1992 | Nagel |
| 5,159,100 A | 10/1992 | Hanselmann |

(Continued)

FOREIGN PATENT DOCUMENTS

| DE | 967826 | 12/1957 |
| WO | 2011136383 A1 | 11/2011 |

(Continued)

OTHER PUBLICATIONS

Cherbuliez et al., "148. Recherches sur la Formation et la Transformation des esters LXXV[1]", Helvetica Chimica Acta, 1967(50) pp. 1440-1452 (English Summary Included).

(Continued)

*Primary Examiner* — Emily Bernhardt
(74) *Attorney, Agent, or Firm* — Shanay M. McCastle

(57) ABSTRACT

Novel processes, and intermediates, for making alkylated arylpiperazine and alkylated arylpiperidine compounds of the general formulas (I) and (VII), respectively

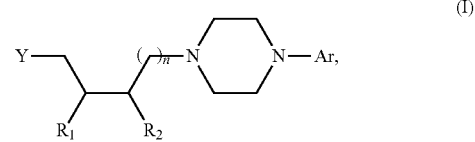

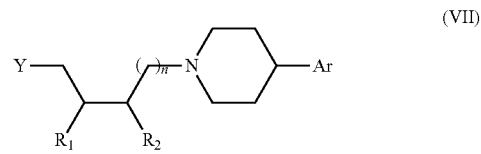

wherein, $R_1$ and $R_2$ are individually selected from hydrogen, alkyl, substituted or alkyl; n=0, 1, or 2; Y=$NR_3R_4$, $OR_5$, or $SR_5$, where $R_3$ and $R_4$ are individually selected from acyl or sulfonyl, and where $R_5$ is aryl or heteroaryl, or heterocyclic; and Ar is an aryl, heteroaryl, or heterocyclic compound.

1 Claim, No Drawings

(51) Int. Cl.
  *C07D 295/135* (2006.01)
  *C07D 409/12* (2006.01)
  *C07D 471/08* (2006.01)

(56) References Cited

U.S. PATENT DOCUMENTS

| | | |
|---|---|---|
| 5,294,619 A | 3/1994 | Nagel |
| 5,532,372 A | 7/1996 | Saji et al. |
| 6,467,121 B1 | 10/2002 | Franzino et al. |
| 7,276,610 B2 | 10/2007 | Huang et al. |
| 7,605,260 B2 | 10/2009 | Kakiya et al. |
| 8,258,139 B2 | 9/2012 | Ikeda et al. |
| 8,258,304 B2 | 9/2012 | Meerpoel et al. |
| 8,283,352 B2 | 10/2012 | Otoda et al. |
| 8,377,995 B2 | 2/2013 | Ikeda et al. |
| 2006/0025422 A1 | 2/2006 | Nakamura et al. |
| 2006/0257987 A1* | 11/2006 | Gonzalez Valcarcel ............ A61K 31/095 435/188 |
| 2007/0160537 A1 | 7/2007 | Ishiyama |
| 2008/0045543 A1 | 2/2008 | Carter et al. |
| 2009/0076027 A1 | 3/2009 | Czarnik |
| 2009/0176800 A1 | 7/2009 | Ishiyama |
| 2011/0237602 A1 | 9/2011 | Meltzer et al. |
| 2011/0263847 A1 | 10/2011 | Ae et al. |
| 2011/0263848 A1 | 10/2011 | Ae et al. |
| 2013/0018056 A1 | 1/2013 | Ikeda et al. |

FOREIGN PATENT DOCUMENTS

| | | |
|---|---|---|
| WO | 2011136384 A1 | 11/2011 |
| WO | 2012063246 A1 | 5/2012 |
| WO | 2012107890 A2 | 8/2012 |
| WO | 2012123858 A1 | 9/2012 |
| WO | 2012131606 A1 | 10/2012 |
| WO | 2012158492 A2 | 11/2012 |
| WO | 2013014665 A1 | 1/2013 |
| WO | 2013014665 A1 | 2/2013 |
| WO | 2013030722 A1 | 3/2013 |

OTHER PUBLICATIONS

Dolenski et al., "Molecules Amphiphiles Electroreductibles. Etude de la Reductio en Milieux de Sulfates d'omega-(4-acetylphenoxy)alkyle", Bull. Soc. Chim. Fr. 1996 (133) pp. 235-242 (English Summary Included).

Nagamura et al., "Novel effect of Man-Made Molecular Assemblies on Photoinduced Charge Separation. 4.Synthetic Bilayer Membrane of Amphipathic Viologen as an Efficient Electron Collector in Photosensitized Redox Reactions", Ber. Bunsenges. Phys. Chem. 1983(87)12 pp. 1129-1133.

Jia et al., "Synthesis and Evaluation of a Novel Class Hsp90 Inhibitors Containing 1-phenylpiperazine Scaffold", Bioorganic & Med. Chem. Letters 2014(24)6 pp. 1557-1561.

Pai et al., "Synthesis of Novel Analogs 3,4-dihydro-1H-1uinolin-2-one Derivatives as Typical Antidepressant, Sedative and Anti-Parksinson Agents", Heterocyclic Letters 2012(2)1 pp. 117-128.

Fischer et al., "Reaktivitaet and Toxizitaet Cyclischer Schwefelsaeur Fester", Journal Fuer Praktische Chemie 1975 (317)6 pp. 943-952 (English Abstract Included).

Lichtenberger, et al., "No 204. Sur Les Sulfates de Diols", Bull. Soc. Chim. Fr. 1948 pp. 1002-1012 (English Abstract Included).

Hassner et al., "EI-Massenspektrometrie N-monosulfoalkyl-substituierte Cyanine", Zeitschrift Fur Chemie 1989(29)2 pp. 65-66 (English Translated Included).

\* cited by examiner

PROCESSES FOR MAKING ALKYLATED ARYLPIPERAZINE AND ALKYLATED ARYLPIPERIDINE COMPOUNDS INCLUDING NOVEL INTERMEDIATES

CROSS-REFERENCE TO RELATED APPLICATIONS

This application claims priority of U.S. Provisional Patent Application No. 62/012,701, filed Jun. 16, 2014, the disclosures of which are incorporated herein by reference in their entireties for all purposes.

FIELD OF THE INVENTION

The present disclosure provides processes for making alkylated arylpiperazine and alkylated arylpiperidine compounds as well as novel intermediate compounds formed during those processes.

BACKGROUND OF THE INVENTION

The piperazines are a broad class of chemical compounds, many with important pharmacological properties, which contain a core piperazine functional group. Many currently notable pharmaceutical drugs contain a piperazine ring as part of their molecular structure. Examples include: anti-anginals (ranolazine, trimetazidine); antidepressants (amoxapine, befuraline, buspirone, flesinoxan, gepirone, ipsapirone, nefazodone, piberaline, tandospirone, trazodone, vilazodone, zalospirone); antihistamines (buclizine, meclozine, cinnarizine, cyclizine, hydroxyzine, cetirizine, levocetirizine, niaprazine); antipsychotics (fluphenazine, perphenazine, trifluoperazine, prochlorperazine, thiothixene, flupentixol, zuclopenthixol, amperozide, aripiprazole, lurasidone, clozapine, olanzapine, perospirone, ziprasidone); urologicals (sildenafil, vardenafil).

Piperidine is also widely used building block and chemical reagent in the synthesis of organic compounds, including pharmaceuticals. Similar to piperazine, piperidine and its derivatives are ubiquitous building blocks in the synthesis of pharmaceuticals and fine chemicals. For example, the piperidine structure is found in the following classes of pharmaceuticals: SSRI (selective serotonin reuptake inhibitors) (paroxetine); analeptics/nootropics (stimulants) (methylphenidate, ethylphenidate, pipradrol, desoxypipradrol); SERM (selective estrogen receptor modulators) (raloxifene); vasodilators (minoxidil); neuroleptics (antipsychotics) (risperidone, thioridazine, haloperidol, droperidol, mesoridazine); opioids (pethidine, meperidine, loperamide).

Considering their prevalence in the formation of a variety of important pharmaceutical compounds, there is a need for new and improved processes for making both piperazine and piperidine compounds, including intermediates and derivatives thereof, that minimizes the formation of unwanted by-products and eliminates the need for additional purification steps where product is lost.

SUMMARY OF THE INVENTION

The present disclosure provides processes for making alkylated arylpiperazine and alkylated arylpiperidine compounds, including intermediates and derivatives thereof. More specifically, the present invention provides processes for making a variety of alkylated arylpiperazine and alkylated arylpiperidine compounds of the general formulas (I) and (VII), respectively,

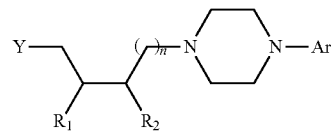

(I)

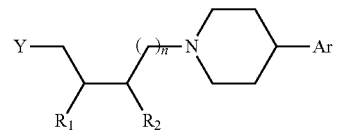

(VII)

wherein, $R_1$ and $R_2$ are individually selected from hydrogen, unsubstituted alkyl, and substituted alkyl, or $R_1$ and $R_2$ are connected to form a 5 to 8 carbon cyclic ring; n is 0, 1, or 2; Y is $NR_3R_4$, $OR_5$, or $SR_5$, where $R_3$ and $R_4$ are individually selected from acyl or sulfonyl, wherein $R_3$ and $R_4$ may be connected to form a substituted or unsubstituted cyclic or bicyclic ring, and wherein $R_5$ is aryl or heteroaryl, or heterocyclic; and Ar is an aryl or heteroaryl group.

Novel intermediate compounds, made during the processes described and claimed herein, are also disclosed.

BRIEF DESCRIPTION OF THE DRAWINGS

No drawings.

DETAILED DESCRIPTION OF THE INVENTION

Definitions

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

All numerical designations, such as, weight, pH, temperature, time, concentration, and molecular weight, including ranges, are approximations which are varied by 10%. It is to be understood, although not always explicitly stated, that all numerical designations are preceded by the term "about." It also is to be understood, although not always explicitly stated, that the reagents described herein are merely exemplary and that equivalents of such are known in the art.

In reference to the present disclosure, the technical and scientific terms used in the descriptions herein will have the meanings commonly understood by one of ordinary skill in the art, unless specifically defined otherwise. Accordingly, the following terms are intended to have the following meanings.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, the term "alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e., $C_1$-$C_6$ alkyl. Examples of alkyl groups include, but are not limited to, methyl, ethyl, propyl, isopropyl, isobutyl, sec-butyl, tert-butyl, pentyl, n-hexyl, octyl, dodecyl, and the like. "Branched alkyl" means, for example, isopropyl, isobutyl, and tert-butyl. Specifically included within the definition of "alkyl" are those aliphatic hydrocarbon chains that are optionally substituted.

As used herein, the term "alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

As used herein, the term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclic or heterocyclic groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

As used herein, the term "heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclic or heterocyclic groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (arylheteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

As used herein, the term "heterocyclic" refers to a radical of a 3 to 10 membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclic"). In heterocyclic groups that contain one or more nitrogen atoms, the point of attachment can be a carbon or nitrogen atom, as valency permits. A heterocyclic group can either be monocyclic ("monocyclic heterocyclic") or a fused, bridged or spiro ring system such as a bicyclic system ("bicyclic heterocyclic"), and can be saturated or can be partially unsaturated. Heterocyclic bicyclic ring systems can include one or more heteroatoms in one or both rings. "Heterocyclic" also includes ring systems wherein the heterocyclic ring, as defined above, is fused with one or more carbocyclic groups wherein the point of attachment is either on the carbocyclic or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclic is independently optionally substituted, i.e., unsubstituted (an "unsubstituted heterocyclic") or substituted (a "substituted heterocyclic") with one or more substituents. In certain embodiments, the heterocyclic group is unsubstituted 3-10 membered heterocyclic. In certain embodiments, the heterocyclic group is substituted 3-10 membered heterocyclic.

In some embodiments, a heterocyclic group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocylic"). In some embodiments, a heterocyclic group is a 5-8 membered non-aromatic ring system having ring carbon atoms and 1-4 ring heteroatoms, wherein each heteroatom is independently selected from nitrogen, oxygen, and sulfur ("5-8 membered heterocyclic"). In some embodiments, a heterocyclic group is a 5-6 membered non-aromatic ring system having ring carbon atoms and 1-4 ring heteroatoms, wherein each heteroatom is independently selected from nitrogen, oxygen, and sulfur ("5-6 membered heterocyclic"). In some embodiments, the 5-6 membered heterocyclic has 1-3 ring heteroatoms selected from nitrogen, oxygen, and sulfur. In some embodiments, the 5-6 membered heterocyclic has 1-2 ring heteroatoms selected from nitrogen, oxygen, and sulfur. In some embodiments, the 5-6 membered heterocyclic has one ring heteroatom selected from nitrogen, oxygen, and sulfur.

Exemplary 3-membered heterocyclic groups containing one heteroatom include, without limitation, azirdinyl, oxiranyl, and thiiranyl. Exemplary 4-membered heterocyclic groups containing one heteroatom include, without limitation, azetidinyl, oxetanyl and thietanyl. Exemplary 5-membered heterocyclic groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclic groups containing two heteroatoms include, without limitation, dioxolanyl, oxasulfuranyl, disulfuranyl, and oxazolidin-2-one. Exemplary 5-membered heterocyclic groups containing three heteroatoms include, without limitation, triazolinyl, oxadiazolinyl, and thiadiazolinyl. Exemplary 6-membered heterocyclic groups containing one heteroatom include, without limitation, piperidinyl, tetrahydropyranyl, dihydropyridinyl, and thianyl. Exemplary 6-membered heterocyclic groups containing two heteroatoms include, without limitation, piperazinyl, morpholinyl, dithianyl, dioxanyl. Exemplary 6-membered heterocyclic groups containing two heteroatoms include, without limitation, triazinanyl. Exemplary 7-membered heterocyclic groups containing one heteroatom include, without limitation, azepanyl, oxepanyl and thiepanyl. Exemplary 8 membered heterocyclic groups containing one heteroatom include, without limitation, azocanyl, oxecanyl and thiocanyl. Exemplary 5-membered heterocyclic groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclic groups fused to an aryl ring (also referred to herein as a 6,6-bicyclic heterocyclic ring) include, without limitation, tetrahydroquinolinyl, tetrahydroisoquinolinyl, and the like.

As used herein, the term "acyl" refers to a radical —C(O)$R^a$, where $R^a$ is hydrogen, substituted or unsubstituted alkyl, substituted or unsubstituted alkenyl, substituted or unsubstituted alkynyl, substituted or unsubstituted carbocyclic, substituted or unsubstituted heterocyclic, substituted or unsubstituted aryl, or substituted or unsubstituted heteroaryl, as defined herein. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—C$_1$-C$_8$ alkyl, —C(O)—(CH$_2$)$_t$(C$_6$-C$_{10}$ aryl), —C(O)—(CH$_2$)$_t$(5-10 membered heteroaryl), —C(O)—(CH$_2$)$_t$(C$_3$-C$_{10}$ cycloalkyl), and —C(O)—(CH$_2$)$_t$(4-10 membered heterocyclic), wherein t is an integer from 0 to 4.

As used herein, the term "alkoxy" refers to the group —OR$^b$ where R$^b$ is substituted or unsubstituted alkyl, substituted or unsubstituted alkenyl, substituted or unsubstituted alkynyl, substituted or unsubstituted carbocyclic, substituted or unsubstituted heterocyclic, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e., with between 1 and 6 carbon atoms. Further particular alkoxy groups have between 1 and 4 carbon atoms.

As used herein, the term "halo" or "halogen" refers to fluoro (F), chloro (Cl), bromo (Br), and iodo (I).

Alkyl, heterocyclic, aryl, and heteroaryl groups, as defined herein, are optionally substituted (e.g., "substituted" or "unsubstituted" alkyl, "substituted" or "unsubstituted" heterocyclic, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Optional substituents for alkyl, alkenyl, aryl, heteroaryl, or heterocycle groups are well known to those skilled in the art. These substituents include alkyl, alkoxy, aryloxy, hydroxy, acetyl, cyano, nitro, glyceryl, and carbohydrate, or two substituents taken together may be linked as an -alkylene-group to form a ring.

As used herein, the term "leaving group" or "LG" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, mesylate, and thienyloxy, dihalophosphinoyloxy, optionally substituted benzyloxy, isopropyloxy, acyloxy, and the like.

Preferred Embodiments of the Process of the Invention

The present invention provides processes for making arylpiperazine and arylpiperidine compounds, including intermediates and derivatives thereof. More specifically, the present invention provides processes or methods for making a variety of alkylated arylpiperazine and alkylated arylpiperidine compounds of the general formulas (I) and (VII), respectively.

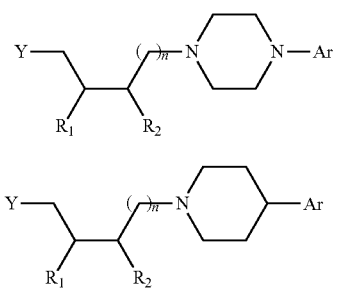

(I)

(VII)

wherein, $R_1$ and $R_2$ are individually selected from hydrogen, unsubstituted alkyl, and substituted alkyl, or $R_1$ and $R_2$ are connected to form a 5 to 8 carbon cyclic ring; n is 0, 1, or 2; Y is $NR_3R_4$, $OR_5$, or $SR_5$, where $R_3$ and $R_4$ are individually selected from acyl or sulfonyl, wherein $R_3$ and $R_4$ may be connected to form a substituted or unsubstituted cyclic or bicyclic ring, and wherein $R_5$ is aryl or heteroaryl, or heterocyclic; and Ar is an aryl or heteroaryl group.

Arylpiperazine compounds of formula (I) include, for example, lurasidone, tiospirone, revospirone, perospirone, brexipirazole, aripiprazole, buspirone, gepirone, ipsapirone, eptapirone, umespirone, tandospirone, and zalospirone.

Arylpiperidine compounds of formula (VII) include, for example, iloperidone and abaperidone.

The processes for making the alkylated arylpiperazine and alkylated arylpiperidine compounds disclosed herein have certain common features and process steps. For example, as shown, the processes for making the alkylated arylpiperazine and alkylated arylpiperidine compounds both comprise the step of alkylating the compound YH with a cyclic sulfate of formula (II) in the presence of a base to form a compound of formula (III) wherein Q is hydrogen, a metal, or an ammonium salt.

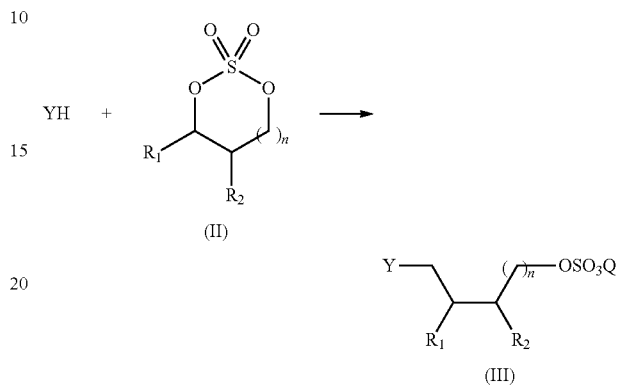

In preferred embodiments, $R_1$ and $R_2$ in formulas (II) and (III) are connected to form a 5 to 8 carbon cyclic ring. Preferably, $R_1$ and $R_2$ are connected to form a 5 or 6 carbon cyclic ring and, most preferably a 6 carbon cyclic aliphatic ring.

In preferred embodiments, the compound YH is a cyclic imide or cyclic amide such that Y is $NR_3R_4$, where $R_3$ and/or $R_4$ are acyl, and wherein $R_3$ and $R_4$ are connected to form a cyclic or bicyclic ring. Preferred compounds that meet the requirements for YH include, for example:

TABLE 1

Representative Compounds of Formula YH

| Entry | YH |
|---|---|
| 1 | (3aR,4S,7R,7aS)-hexahydro-1H-4,7-methanoisoindole-1,3(2H)-dione |
| 2 | 1-(3-hydroxy-4-methoxyphenyl)ethan-1-one |

TABLE 1-continued

Representative Compounds of Formula YH

| Entry | YH |
|---|---|
| 3 | 8-azaspiro[4.5]decane-7,9-dione |
| 4 | benzo[d]isothiazol-3(2H)-one 1,1-dioxide |
| 5 | (3aR,7aS)-hexahydro-1H-isoindole-1,3(2H)-dione |
| 6 | 7-hydroxyquinolin-2(1H)-one |
| 7 | 4,4-dimethylpiperidine-2,6-dione |
| 8 | N-(4-hydroxy-3-methoxyphenyl)acetamide |
| 9 | 4-methyl-1,2,4-triazine-3,5(2H,4H)-dione |
| 10 | 3-butyl-9,9-dimethyl-3,7-diazabicyclo[3.3.1]nonane-2,4,6,8-tetraone |
| 11 | (3aR,4aR,6aS,7aS)-3a,4,4a,6a,7,7a-hexahydro-1H-4,7-ethenocyclobuta[f]isoindole-1,3(2H)-dione |
| 12 | 3-(hydroxymethyl)-7-methoxy-4H-chromen-4-one |
| 13 | quinazoline-2,4(1H,3H)-dione |

TABLE 1-continued

Representative Compounds of Formula YH

| Entry | YH |
|---|---|
| 14 | 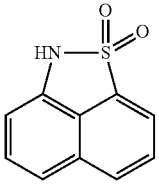<br>2H-naphtho[1,8-cd]isothiazole 1,1-dioxide |
| 15 | 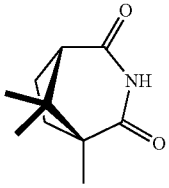<br>1,8,8-trimethyl-3-azabicyclo[3.2.1]octane-2,4-dione |
| 16 | 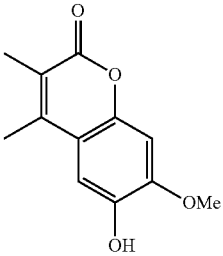<br>6-hydroxy-7-methoxy-3,4-dimethyl-2H-chromen-2-one |

In a preferred embodiment of the present invention, YH is:

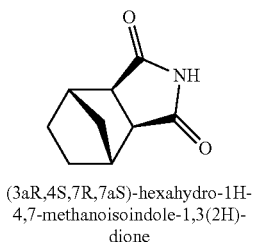 [SMILES: O=C1NC(=O)[C@H]2[C@@H]3CC[C@@H](C3)[C@@H]12]

(3aR,4S,7R,7aS)-hexahydro-1H-4,7-methanoisoindole-1,3(2H)-dione

In the reaction between compound YH and the cyclic sulfate of formula (II) in the present invention, compound YH is preferably present in the reaction mixture in an amount of from about 1.0 to 2.0 equivalents and, more preferably, from about 1.1 to 1.2 equivalents based on the amount of the cyclic sulfate of formula (II).

The alkylation reaction according to the present invention is preferably carried out in a suitable solvent at a temperature of from about 20° C. to about 120° C. in the presence of a base.

Suitable solvents for this step include, but are not limited to, hydrocarbons, halogenated hydrocarbons, aromatic hydrocarbons, esters, ethers, nitriles, ketones, and mixtures thereof. In preferred embodiments, the solvent is acetonitrile.

Suitable bases for this step include alkali metal carbonates such as potassium carbonate, sodium carbonate, calcium carbonate, and magnesium carbonate; alkali metal bicarbonates such as sodium bicarbonate, and potassium bicarbonate; preferably an alkali metal carbonate, in particular, potassium carbonate; alkali metal hydroxides such as sodium hydroxide, potassium hydroxide, magnesium hydroxide, or calcium hydroxide; alkali metal phosphates such as sodium phosphate or potassium phosphate; and organic amine bases such as triethylamine, diisopropylethylamine and pyridine. Ammonium salts of the above bases are also suitable. Solid inorganic bases may be used alone or as a mixture of two or more kinds of bases, and may be an anhydrous form or a hydrate thereof. In preferred embodiments, the base employed for this step is potassium carbonate, $K_2CO_3$.

The amount of the base used herein is generally about 0.7 mole or more, preferably 1.0 mole or more, per one mole of the total amount of compound YH. The upper limit amount of the solid inorganic base used herein is not limited but an excess amount of base can increase process costs. Accordingly, a practical amount of solid inorganic base is 10 mole or less, preferably 2.0 mole or less, per one mole of the total amount of compound YH.

The progress of the alkylation reaction in the present invention can be monitored by any means known to those skilled in the art such as, for example, gas chromatography (GC) or high performance liquid chromatography (HPLC).

The compound of formula (III) may be isolated by any method known to those skilled in the art. In preferred embodiments, however, the compound of formula (III) is not isolated from the reaction mixture in which it was formed, but rather is telescoped. In this regard, the compound of formula (III) may be readied for a hydrolysis step by the addition of water, which generates a clean phase split with, for example, acetonitrile due to the solubilized base such as, for example, potassium carbonate, without significant product loss. The organic solvent layer is then preferably washed further with aqueous NaCl in a conventional extraction process to remove any residual carbonate prior to a hydrolysis reaction.

An unexpected benefit of employing a cyclic sulfate of formula (II) in the process of the present invention is that it leads to the advantageous selective monoalkylation of the cyclic sulfate without the possibility of double alkylation. The anionic ring-opened sulfate (after initial alkylation) is not prone to further displacement by nucleophiles. Thus, after conversion of the alcohol to a suitable leaving group, simple displacement chemistry is employed to provide the final product. In other words, the process of the present invention produces alkylated arylpiperazine and alkylated arylpiperidine compounds wherein no bis-imide product is detected in the alkylation of the cyclic sulfate.

The process for making the alkylated arylpiperazine and arylpiperidine derivative compounds according to the present invention also comprises the step of hydrolyzing a compound of formula (III) to form an alcohol of formula (IV) as shown here.

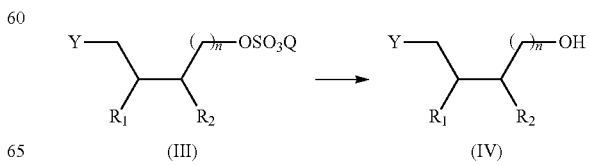

In this reaction step, aqueous acid is added to a washed organic solvent layer containing the compound of formula (III) and the mixture is agitated at a temperature of from about 20° C. to about 100° C. During this step, the sulfate ester moiety of the compound of formula (III) is hydrolyzed to an alcohol group (—OH). In some embodiments, an additional solvent such as, for example, toluene, may be added to the mixture prior to the aqueous acid.

The progress of the hydrolysis reaction in the present invention can be monitored by any means known to those skilled in the art such as, for example, high performance liquid chromatography (HPLC).

Preferably, once the reaction is complete, the organic phase is cooled and the organic phase is prepared for another step in the process of the present invention. This preparation typically involves washing several times with water employing a conventional extraction process. The organic phase may also be distilled under vacuum followed by addition of the desired solvent for the next step of the process. An example of such solvent is toluene.

The process of the present invention for making alkylated arylpiperazine and alkylated arylpiperidine compounds also comprises a step of converting the compound of formula (IV) to an alkylating agent of formula (V) wherein LG is a leaving group.

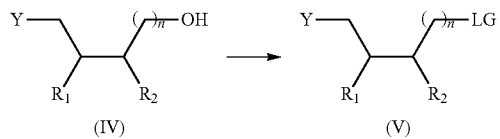

In the compound of formula (V), preferably LG is selected from the group consisting of an aryl sulfonate, alkyl sulfonate, phosphate, phosphonate, proazaphosphatrane and a halogen. In preferred embodiments, LG is a mesylate.

The conversion of the hydroxyl group to one of the recited leaving groups can be effected by any means known to one skilled in the art. In preferred embodiments where LG is a mesylate, for example, it was found that the conversion can occur quickly and effectively in a mixture of toluene and a base such as, for example, triethylamine. In this embodiment, about 1.2 equivalents of methanesulfonyl chloride relative to the alcohol is added to the mixture to initiate the reaction. Other suitable solvents for this step include, for example, hydrocarbons, halogenated hydrocarbons, aromatic hydrocarbons, esters, ethers, nitriles, ketones, and mixtures thereof.

The progress of the conversion reaction in the present invention can be monitored by any means known to those skilled in the art such as, for example, HPLC. Such a reaction typically requires from about 0.5 hours to about 12 hours for completion, depending on variables such as, for example, temperature, equivalents of activating agent, and concentration of the reactants. For example, the less solvent employed the faster the reaction is likely to proceed.

Once the reaction is complete, the mixture is preferably washed with water. The aqueous layer can then be separated and removed following the wash. Preparation of the organic phase for the next step in the process of the present invention can be accomplished by vacuum distillation until the desired volume is reached.

The process of making alkylated arylpiperazine compounds according to the present invention comprises a step of alkylating a piperazine compound of formula (VI) with an alkylating agent of formula (V) to provide the alkylated arylpiperazine of formula (I).

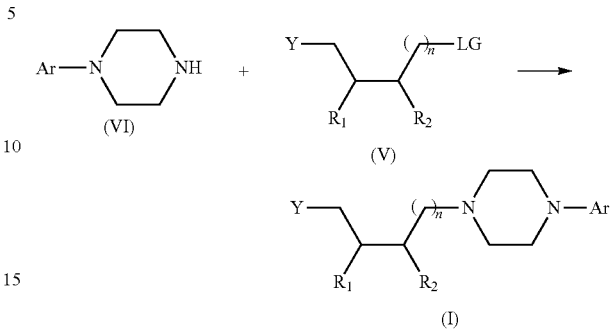

In the reaction between the compounds of formula (V) and (VI) in the present invention, the compound of formula (VI) is preferably present in the reaction mixture in an amount of from 1.0 to 10.0 equivalents and, more preferably, from 1.1 to 1.2 equivalents based on the amount of the compound of formula (V). Also present in the reaction is about 1.5 equivalents of a base. Suitable bases for this step include alkali metal carbonates such as potassium carbonate, sodium carbonate, calcium carbonate, and magnesium carbonate; alkali metal bicarbonates such as sodium bicarbonate, and potassium bicarbonate; preferably an alkali metal carbonate, in particular, potassium carbonate; alkali metal hydroxides such as sodium hydroxide, potassium hydroxide, magnesium hydroxide, or calcium hydroxide; alkali metal phosphates such as sodium phosphate or potassium phosphate; and organic amine bases such as triethylamine, diisopropylethylamine and pyridine. Ammonium salts of the above bases are also suitable. Solid inorganic bases may be used alone or as a mixture of two or more kinds of bases, and may be an anhydrous form or a hydrate thereof. In preferred embodiments, the base employed for this step is potassium carbonate, $K_2CO_3$. The amount of the base used herein is generally about 0.7 mole or more, preferably 1.0 mole or more, per one mole of the total amount of compound of formula (VI). The upper limit amount of the solid inorganic base used herein is not limited, but, in case that the amount is too much, the process cost increases. Accordingly, a practical amount of the base is 3 mole or less, preferably 2.0 mole or less, per one mole of the total amount of compound of formula (VI).

The progress of the reaction can be monitored by any means known to those skilled in the art such as, for example, HPLC.

Once complete, the reaction mixture is preferably cooled followed by addition of solvent. The aqueous layer is removed followed by additional washes of the organic phase with water. Once the aqueous layer is separated, the organic layer is preferably distilled under vacuum and an antisolvent is added. Suitable antisolvents for this step include, but are not limited to, hydrocarbons, halogenated hydrocarbons, aromatic hydrocarbons, esters, ethers, nitriles, ketones, and mixtures thereof. To effect crystallization of the arylpiperazine of formula (I), the mixture is preferably successively heated and cooled in the mixture of solvent and antisolvent.

The process of making alkylated arylpiperidine compounds according to the present invention comprises a step of alkylating an arylpiperidine compound of formula (VIII) with an alkylating agent of formula (V) to provide the alkylated arylpiperidine of formula (VII).

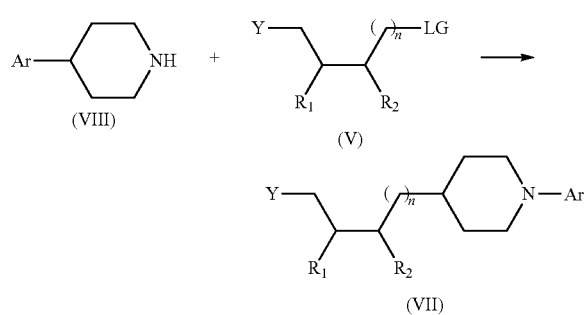

The reaction conditions and product separation are about the same as those described above regarding the alkylated arylpiperazine compounds.

As will be understood by those of ordinary skill in the art, the processes described above and herein can be employed to produce a variety of compounds. For example, as shown in Table 2 below, the following compounds can be made by the process described herein for making the alkylated arylpiperazine compound of formula (I).

TABLE 2

Compounds of Formula (I)

| Compound Name | Structure | R1 | R2 | n | YH | Ar |
|---|---|---|---|---|---|---|
| Lurasidone | 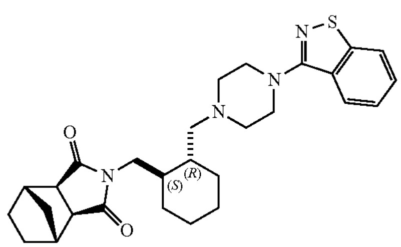 | —((CH$_2$)$_4$)— | NA | 2 | (3aR,4S,7R,7aS)-hexahydro-1H-4,7-methanoisoindole-1,3(2H)-dione | 3-benzo[d]isothiazolyl |
| Tiospirone | 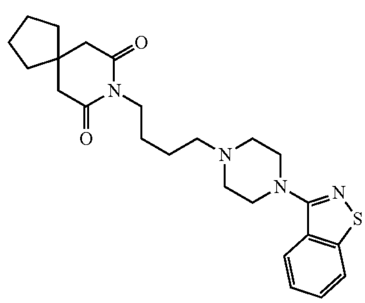 | H | H | 2 | 8-azaspiro[4.5]decane-7,9-dione | 3-benzo[d]isothiazolyl |
| Revospirone | 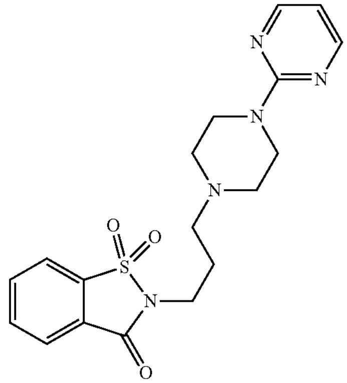 | H | H | 1 | benzo[d]isothiazol-3(2H)-one 1,1-dioxide | 2-pyrimidinyl |

TABLE 2-continued

Compounds of Formula (I)

| Compound Name | Structure | R1 | R2 | n | YH | Ar |
|---|---|---|---|---|---|---|
| Aripiprazole Lauroxil | 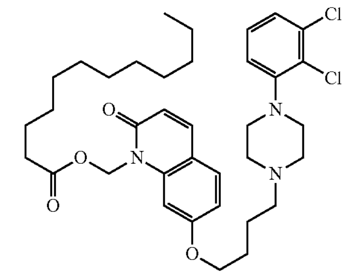 | H | H | 2 | 7-hydroxyquinolin-2(1H)-one | 2,3-dichlorophenyl |
| Buspirone | 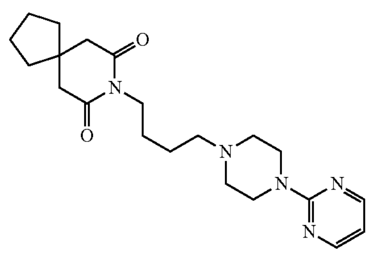 | H | H | 2 | 8-azaspiro[4.5]decane-7,9-dione | 2-pyrimidinyl |
| Gepirone | 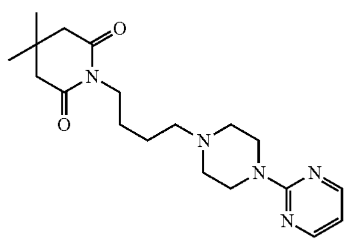 | H | H | 2 | 4,4-dimethylpiperidine-2,6-dione | 2-pyrimidinyl |
| Ipsapirone | 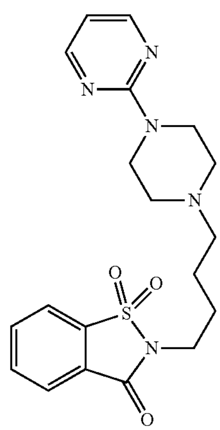 | H | H | 2 | benzo[d]isothiazol-3(2H)-one 1,1-dioxide | 2-pyrimidinyl |
| Eptapirone | 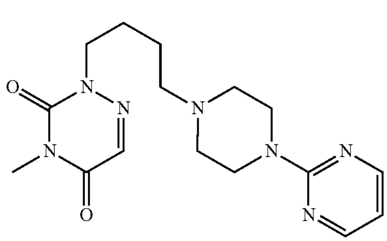 | H | H | 2 | 4-methyl-1,2,4-triazine-3,5-(2H,4H)-dione | 2-pyrimidinyl |

TABLE 2-continued

Compounds of Formula (I)

| Compound Name | Structure | R1 | R2 | n | YH | Ar |
|---|---|---|---|---|---|---|
| Umespirone | 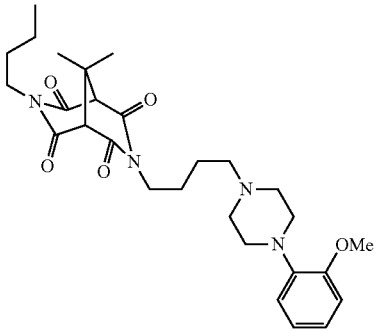 | H | H | 2 | 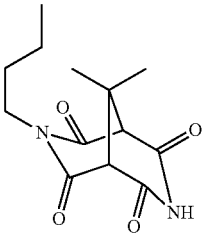<br>3-butyl-9,9-dimethyl-3,7-diazabicyclo[3.3.1]nonane-2,4,6,8-tetraone | 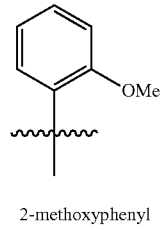<br>2-methoxyphenyl |
| Zalospirone | 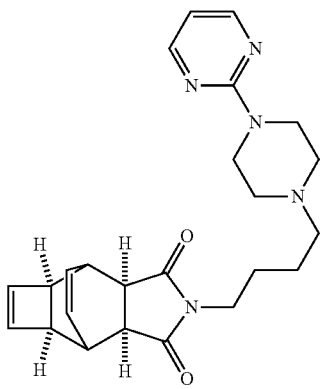 | H | H | 2 | 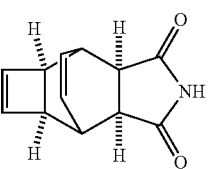<br>(3aR,4aR,6aS,7aS)-3a,4,4a,6a,7,7a-hexahydro-1H-4,7-ethenocyclobuta[f]isoindole-1,3(2H)-dione | 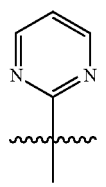<br>2-pyrimidinyl |
| Pelanserin | 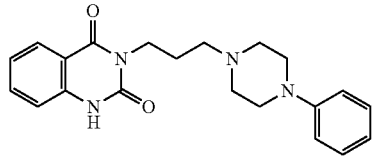 | H | H | 1 | 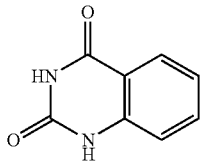<br>quinazoline-2,4(1H,3H)-dione | 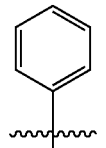<br>phenyl |
| Fananserin | 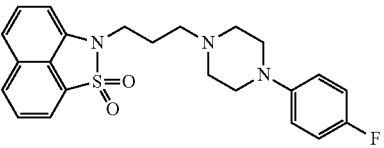 | H | H | 1 | 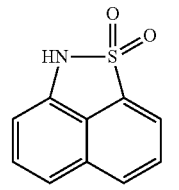<br>2H-naphtho[1,8-cd]-isothiazole 1,1-dioxide | 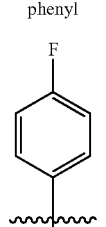<br>4-fluorophenyl |
| Piricapiron | 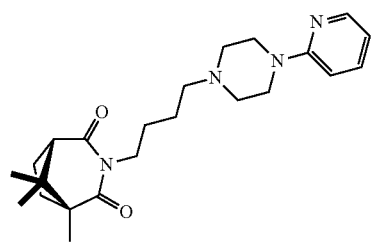 | H | H | 2 | 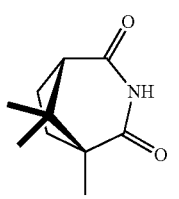<br>1,8,8-trimethyl-3-azabicyclo[3.2.1]octane-2,4-dione | 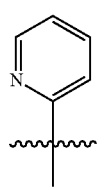<br>2-pyridyl |

TABLE 2-continued

Compounds of Formula (I)

| Compound Name | Structure | R1 | R2 | n | YH | Ar |
|---|---|---|---|---|---|---|
| OPC-4392 | 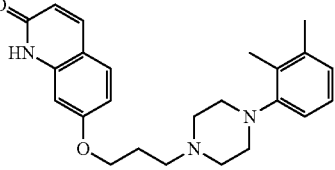 | H | H | 1 | 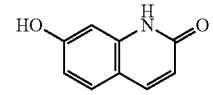<br>7-hydroxyquinolin-2(1H)-one | 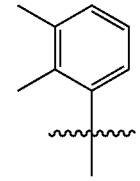 [SMILES: *c1cccc(C)c1C]<br>2,3-dimethylphenyl |
| Mafoprazine | 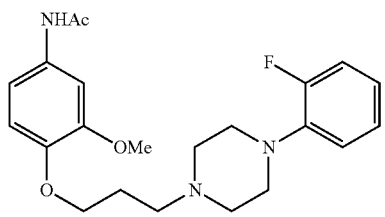 | H | H | 1 | 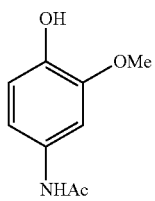<br>N-(4-hydroxy-3-methoxyphenyl)acetamide | 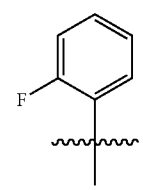<br>2-fluorophenyl |
| Enasculin | 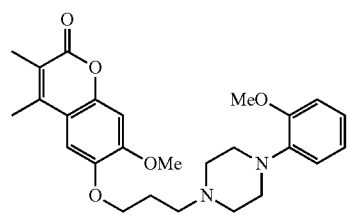 | H | H | 1 | 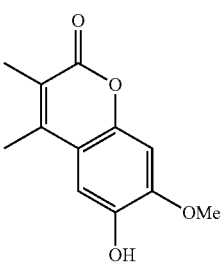<br>6-hydroxy-7-methoxy-3,4-dimethyl-2H-chromen-2-one | 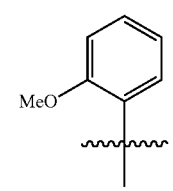 [SMILES: *c1ccccc1OC]<br>2-methoxyphenyl |

Similarly, as shown in Table 3 below, the following compounds can be made by the process described herein for making the alkylated arylpiperidine compounds of formula (VII).

TABLE 3

Compounds of Formula (VII)

| Compound Name | Structure | R1 | R2 | n | YH | Ar |
|---|---|---|---|---|---|---|
| Iloperidone | 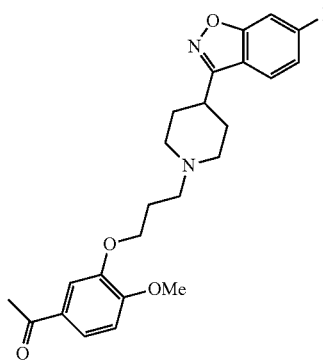 | H | H | 1 | 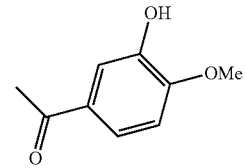<br>1-(3-hydroxy-4-methoxyphenyl)ethan-1-one | 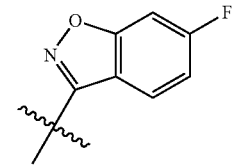 [SMILES: *c1noc2cc(F)ccc12]<br>6-fluoro-3-benzo[d]isoxazolyl |

TABLE 3-continued

Compounds of Formula (VII)

| Compound Name | Structure | R1 | R2 | n | YH | Ar |
|---|---|---|---|---|---|---|
| Abaperidone | 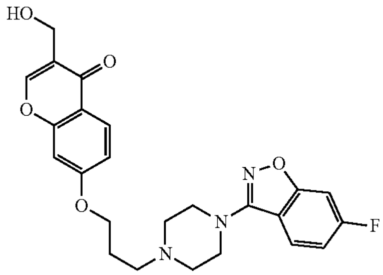 | H | H | 1 | 3-(hydroxymethyl)-7-methoxy-4H-chromen-4-one | 6-fluoro-3-benzo[d]isoxazolyl |

In the process of making the alkylated arylpiperazine and alkylated arylpiperidine compounds disclosed herein, numerous intermediate compounds are produced.

The following examples illustrate various aspects of the present invention.

EXAMPLES

Example 1

Telescoped Preparation of (5aR,9aR)-octahydrobenzo[e][1.3.2]dioxathiepine 3,3-dioxide

[(1R,2R)-cyclohexane-1,2-diyl]dimethanol (mol. wt. 144.21) is added to acetonitrile providing a reaction mixture in the form of a suspension. The mixture is stirred and cooled to 0-5° C. Thionyl chloride is added to the mixture at a temperature of 0-10° C. which results in a clear solution. The solution is stirred at 0-5° C. and assayed periodically to confirm completion of the reaction.

In a separate vessel, an aqueous solution of potassium bicarbonate (2.5 eq) is added prepared and then cooled to 0-5° C. The completed reaction solution above is then quenched into the aqueous potassium bicarbonate solution. The batch is then warmed to 20-25° C. and the upper acetonitrile layer is separated and collected. The aqueous layer is extracted with acetonitrile and the organic layers are combined resulting in a solution of (5aR,9aR)-octahydrobenzo[e][1,3,2]dioxathiepine 3-oxide (mol. wt. 190.26).

In a separate vessel, 50% ruthenium oxide hydrate (0.1 wt. %) and sodium periodate (1.1 eq.) are slurried in water (and EtOAc at 20-25° C. The (5aR,9aR)-octahydrobenzo[e][1,3,2]dioxathiepine 3-oxide solution above is then added to the sodium periodate/ruthenium oxide slurry while maintaining the temperature at ≤30° C. After the reaction is complete, the batch is then filtered, after which the filter cake is washed with EtOAc. The upper organic layer is collected and washed with 20% aqueous sodium chloride. The organic layer is distilled to a minimum volume after which isopropanol is added to the distillate. The resulting slurry is heated to 40-45° C. after which it is cooled to 0-5° C., and then filtered. The solids are washed with isopropanol and dried in a vacuum oven resulting in (5aR,9aR)-octahydrobenzo[e][1,3,2]dioxathiepine 3,3-dioxide (mol. wt. 206.26).

Example 2

Telescoped Preparation of Lurasidone Free Base

Acetonitrile is added to a mixture of (5aR,9aR)-octahydrobenzo[e][1,3,2]dioxathiepine 3,3-dioxide (mol. wt. 206.26, 1 eq.), (3aR,4s,7R,7aS-hexahydro-1H-7,4-methanoisoindole-1,3(2H)-dione (mol. wt. 165.19, 1.2 eq.) and potassium carbonate (2 eq.) and the mixture is heated to about 75° C.

After the reaction is complete, the mixture is cooled to 20-25° C. and water is added to the mixture. A lower, aqueous phase is then removed and an upper, organic phase is washed with aqueous sodium chloride.

The aqueous phases are combined and extracted with acetonitrile. The organic phases are combined to form a solution of potassium ((1R,2R)-2 (((3aR,4S,7R,7aS)-1,3-dioxooctahydro-2H-4,7-methanoisoindol-2-yl)methyl) cyclohexyl)methyl sulfate (mol. wt. 409.54) in acetonitrile which is then distilled to approximately 5 volumes. Toluene is added to the batch and, separately a solution of sulfuric acid (0.5 eq.) and water (0.6 volumes) is prepared. The sulfuric acid solution is added to the batch. This mixture is then heated to approximately 75° C. and the reaction is monitored by HPLC.

Once the reaction is complete, it is cooled to approximately 45° C. and washed twice with water (4 volumes). The aqueous layer is then removed and the organic layer is washed with 5% aqueous $KHCO_3$ (4 volumes) followed by two additional water washes (4 volumes). The organic solution comprising (3aR,4S,7R,7aS)-2-(((1R,2R)-2-(Hydroxymethyl)cyclohexyl)methyl)hexahydro-1H-4,7-methanoisoindole-1,3(2H)-dione (mol. wt. 291.39) is distilled under vacuum to approximately 4 volumes and toluene is added to the batch. This solution is distilled to approximately 4 volumes and toluene is added. This batch is cooled to about 0-5° C., and triethylamine (1.5 eq.) is added after which methanesulfonyl chloride (1.2 eq.) is added. The progress of this reaction is monitored by HPLC.

Once the reaction is complete, water (3 volumes) is added. The aqueous layer is removed and the organic layer is washed with water (2×3 volumes).

The toluene solution of ((1R,2R)-2-(((3aR,4S,7R,7aS)-1,3-dioxooctahydro-2H-4,7-methanoisoindol-2-yl)methyl)cyclohexyl)methyl methanesulfonate is distilled to about 4 volumes under vacuum, and this solution is added to a mixture of 3-(piperazin-1-yl)benzold]isothiazole (1.1 eq.) and $KHCO_3$ (1.5 eq.). Water (1.8 volumes) is added and the mixture is heated to approximately 90° C. The progress of the reaction is monitored by HPLC.

Once the reaction is complete, the batch is cooled to 45±5° C. and toluene (4.5 volumes), water (3.25 volumes), and IPA (1.75 volumes) are added. The aqueous layer is removed and the organic layer is washed with water (2×2.5 volumes) at 40±5° C. The organic layer is distilled under reduced pressure to 3.5 volumes at 50-60° C., then isopropanol (8 volumes) is added. The batch is distilled to 3.5 volumes, then IPA (2.5 volumes) is added. The slurry is heated to 80±5° C. for 1-2 hours, then cooled to 0-5° C. and filtered. The solids are washed with IPA and dried to isolate (3aR,4S,7R,7aS)-2-(((1R,2R)-2-((4-(benzol[d]isothiazol-3-yl)piperazin-1-yl)methylcyclohexyl)methyl) hexahydro-1H-4,7-methanoisoindole-1,3(2H)-dione (lurasidone free base, mol. wt. 492.68).

Example 3

Crystallization of Lurasidone Free Base

The crude lurasidone free base of Example 2 is slurried in ethyl acetate (10 volumes) and heated until a clear solution is obtained. The solution is cooled to 50-55° C. and filtered to remove any particulates in the solution. The solution is further distilled to approximately 4-5 volumes and then cooled to approximately 0-5° C. The resulting solid precipitate is filtered, rinsed with ethyl acetate and then dried under vacuum to provide crystalline lurasidone free base.

Example 4

Preparation of Lurasidone Hydrochloride

The lurasidone free base of Example 3 is slurried in isopropanol (1 eq. base to 15 volumes of isopropanol). The slurry is then heated until a clear solution results. The solution is filtered to remove any particulates in the solution. A pre-filtered solution of 10% aqueous HCl is then added, and the batch is slowly cooled to approximately 45-70° C. until crystals begin to precipitate. The batch is held at this point for several hours, then further cooled to approximately 0° C. The resulting solid precipitate is filtered and then washed with isopropanol (3×2 volumes). The precipitate is dried to provide lurasidone hydrochloride.

Example 5

Telescoped Preparation of
(3-(5-acetyl-2-methoxyphenoxy)propyl
methanesulfonate towards Iloperidone A mixture of 1,3,2-dioxathiane 2,2-dioxide (22.4 g, 160 mmol, 1 eq.), 1-(3-hydroxy-4-methoxyphenyl)ethan-1-one (26.9 g, 160 mmol, 1 eq.) and potassium carbonate (44.8 g, 320 mmol, 2 eq.) in acetonitrile (220 mL) is heated at about reflux temperature. The reaction is monitored by HPLC. Upon completion, the batch is cooled to about 20-25° C. The reaction mixture is filtered through a Celite pad and the pad is washed with acetonitrile (180 mL) to give a solution of potassium 3-(5-acetyl-2-methoxyphenoxy)propyl sulfate in acetonitrile, which is used in the next step.

A solution of $H_2SO_4$ (10 mL $H_2SO_4$ in 90 mL water) is added slowly to the above acetonitrile solution. The batch is then heated to about reflux; the reaction is monitored by HPLC. Upon completion, the reaction mixture is cooled to about 20-25° C., and the resulting phases separated. The organic phase is washed with brine (100 mL×2) and divided into 2 portions (80 mL and 320 mL).

The 80 mL portion from the above reaction is worked up to provide a reference marker of 1-(3-(3-hydroxypropoxy)-4-methoxyphenyl)ethan-1-one as follows. The solvent is removed under reduced pressure to give the crude product, which is purified by column chromatography on silica gel (10× silica gel relative to crude product, petroleum ether:ethyl acetate [2:1] to petroleum ether:ethyl acetate [1:1]) to give 1-(3-(3-hydroxypropoxy)-4-methoxyphenyl)ethan-1-one in 99% purity (2.3 g, white solid).

A large portion of the acetonitrile solution of potassium 3-(5-acetyl-2-methoxyphenoxy)propyl sulfate (320 mL) is progressed forward as follows. Approximately 80% of the solvent is removed, and then ethyl acetate (200 mL) is added. About 80% of the solvent is removed again to give a concentrated solution of 1-(3-(3-hydroxypropoxy)-4-methoxyphenyl)ethan-1-one in ethyl acetate for the next step.

Triethylamine (75 g) and ethyl acetate (200 mL) are added to the above solution, then a solution of $Ms_2O$ (40 g) in ethyl acetate (200 mL) is added dropwise at less than 15° C. The mixture is stirred at about 10° C. overnight. The reaction is monitored by HPLC. Aqueous sodium hydroxide (15%, 250 mL) is added when the reaction is completed, and the mixture is stirred at about 20-25° C. for 15 min. The separated organic layer is then washed with 2 M HCl (200 mL) and brine (200 mL). The solvent is removed under reduced pressure to give the crude product (3-(5-acetyl-2-methoxyphenoxy)propyl methanesulfonate as an off-white solid (15 g, 90% AUC by HPLC).

Example 6

Preparation of Iloperidone Free Base

A mixture of 3-(5-acetyl-2-methoxyphenoxy)propyl methanesulfonate (3 g, 10 mmol, 1 equiv), 6-fluoro-3-(piperidin-4-yl)benzo[d]isoxazole (2.42 g, 11 mmol, 1.1 equiv), $KHCO_3$ (1.5 g, 15 mmol, 1.5 equiv), $H_2O$ (6 g) and toluene (15 mL) is heated at reflux temperature for 12-16 h. Once the reaction is complete, the batch is cooled to about 20-25° C., and then toluene (15 mL), IPA (10 mL) and water (10 mL) are added. The biphasic solution is stirred for about 15 min at about 20-25° C. The organic layer is separated and washed with water (2×10 mL). The batch is concentrated to about 3-4 volumes under vacuum at <50° C. to precipitate an off-white solid. Isopropanol (20 mL) is added, the batch is concentrated to 3-4 volumes under vacuum at <50° C. Isopropanol (20 mL) is added again, and the batch is concentrated to 3-4 volumes under vacuum at <50° C. Isopropanol (10 mL) is added once again and the batch is heated at reflux temperature for 1 h, and then the mixture is cooled to 5-8° C. over 4 h. The mixture is filtered; the cake is washed with isopropanol (2×5 mL) and dried to give Iloperidone free base (3.1 g, 74% yield, 98% AUC by HPLC).

Example 7

Preparation of Potassium 4-(1,1-dioxido-3-oxobenzo[d]isothiazol-2(3H)-yl)butyl sulfate towards Ipsapirone A mixture of benzo[d]isothiazol-3(2H)-one 1,1-dioxide (16.0 g, 87.3 mmol, 1.0 eq.), 1,3,2-dioxathiepane 2,2-dioxide (15.3 g, 100.5 mmol, 1.2 eq.), $K_2CO_3$ (24.1 g, 174.6 mmol, 2.0 eq.) and ACN (240 mL) is heated at reflux temperature for 20 h. After the reaction is complete, the mixture is filtered and concentrated under vacuum to give an oily product. To the residue is added ACN (200 mL), and a solid is precipitated immediately. The mixture is stirred for 1 h at 20-25° C., then filtered. Potassium 4-(1,1-dioxido-3- oxobenzo[d]isothiazol-2(3H)-yl)butyl sulfate is collected as a white solid (11.4 g, 35% yield, 98.5% AUC by HPLC); LC-MS, M+: 335.6 (sulfonic acid).

Example 8

Preparation of
2-(4-hydroxybutyl)benzo[d]isothiazol-3(2H)-one
1,1-dioxide towards Ipsapirone A solution of $H_2SO_4$ (0.8 g, 8.2 mmol, 0.5 eq.) in $H_2O$ (2 mL) is added to a mixture of potassium 4-(1,1-dioxido-3-oxobenzo[d]isothiazol-2(3H)-yl)butyl sulfate (6.1 g, 16.3 mmol, 1.0 eq.) in ACN (90 mL) and $H_2O$ (5 mL) dropwise. The resulting mixture is heated at 75-80° C. until the reaction is deemed complete by HPLC analysis. The mixture is filtered, and filtrate is concentrated to approximately to 10 mL. To the residue, dichloromethane and DI water are added. The layers are separated and the organic layer is washed with saturated $NaHCO_3$ solution, dried over sodium sulfate and then concentrated to give the crude product in 94% purity by HPLC. The crude material is further purified by silica gel column chromatography (petroleum ether:ethyl acetate 4:1 to 3:1) to provide 2-(4-hydroxybutyl)benzo[d]isothiazol-3(2H)-one 1,1-dioxide as a light yellow oil in (2.3 g, 55% yield, 99% AUC by HPLC); LC-MS, M*: 255.8.

Example 9

Preparation of 4-(1,1-dioxido-3-oxobenzo[d]isothiazol-2(3H)-yl)butyl methanesulfonate towards Ipsapirone To a mixture of 2-(4-hydroxybutyl)benzo[d]isothiazol-3(2H)-one 1,1-dioxide (17.2 g, 67.4 mmol, 1.0 eq.) in ethyl acetate (172 mL, 10 vol), is added triethylamine (13.6 g, 134.7 mmol, 2.0 eq.) at <5° C., followed by dropwise addition of $Ms_2O$ (12.9 g, 74.1 mmol, 1.1 eq.) in ethyl acetate (20 mL) at 5-15° C. The mixture is stirred at 20-25° C. for 20 h and the reaction is deemed complete by HPLC. The mixture is washed with $H_2O$ twice, then dried over $Na_2SO_4$. The solvent is removed under reduced pressure to obtain crude material. The crude product is purified by column chromatography on silica gel (30× silica gel, petroleum ether:ethyl acetate [10:1] to petroleum ether ethyl acetate [4:1]) which gives 4-(1,1-dioxido-3-oxobenzo[d]isothiazol-2(3H)-yl)butyl methanesulfonate as a white solid (8.5 g, 38% yield, 96% AUC by HPLC); LC-MS, M+: 355.6.

Example 10

Preparation of Ipsapirone Free Base

A suspension of (1,1-dioxido-3-oxobenzo[d]isothiazol-2 (3H)-yl)butyl methanesulfonate (4.6 g, 13.8 mmol, 1.0 eq), 2-(piperazin-1-yl)pyrimidine (2.9 g, 17.9 mmol, 1.3 eq.), $KHCO_3$ (2.1 g, 20.7 mmol, 1.5 eq.) and toluene (46 mL) is heated at 95-100° C. for 22 h. Deionized water (35 mL) is added, and the organic phase is separated. The aqueous phase is extracted with ethyl acetate (2×30 mL). The organic phases are combined and dried over $Na_2SO_4$. The solvent is removed under reduced pressure to give the crude product, which is purified by column chromatography on silica gel by elution with 17-33% EtOAc/petroleum ether to offer ipsapirone free base as an off-white solid (2 g, 27% yield, 96% AUC by HPLC).

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

What is claimed is:

1. A process for preparing lurasidone comprising the steps of:
    (i) alkylating (3aR,4S,7R,7aS)-hexahydro-1H-4,7-methanoisoindole-1,3(2H)-dione by reacting it with (5aR, 9aR)-octahydrobenzo[e][1,3,2]dioxathiepine-3,3-dioxide in the presence of $K_2CO_3$ to form potassium ((1R, 2R)-2-(((3aR,4S,7R,7aS)-1,3-dioxooctahydro-2H-4,7-methanoisoindol -2-yl)methyl)cyclohexyl)methyl sulfate;
    (ii) hydrolyzing potassium ((1R,2R)-2-(((3 aR,4S,7R,7 aS)-1,3 -dioxooctahydro-2H-4,7-methanoisoindol -2-yl)methyl)cyclohexyl)methyl sulfate to form (3aR, 4S,7R,7aS)-2-(((1R,2R)-2-(hydroxymethyl) cyclohexyl)methyl) hexahydro-1H-4,7-methanoisoindole-1,3 (2H)-dione;
    (iii) reacting (3aR,4S,7R,7aS)-2-(((1R,2R)-2-(hydroxymethyl)cyclohexyl)methyl) hexahydro-1H-4,7-methanoisoindole-1,3(2H)-dione with methanesulfonyl chloride to form ((1R,2R)-2-(((3 aR,4S,7R,7aS)-1,3-dioxooctahydro-2H-4,7-methanoisoindol-2-yl) methyl) cyclohexyl)methyl methanesulfonate; and
    (iv) reacting 3-(piperazin-1-yl)benzo[d]isothiazole with ((1R,2R)-2-(((3aR,4S,7R,7aS)- 1,3-dioxooctahydro-2H-4,7-methanoisoindol-2-yl)methyl)cyclohexyl) methyl methanesulfonate to form (3 aR,4S,7R,7aS)-2 ((((1R,2R)-2-((4-(benzo[d]isothiazol-3-yl)piperazin-1-yl) methyl)cyclohexyl)methyl)hexahydro-1H-4,7-methanoisoindole-1,3(2H)-dione (Lurasidone).

* * * * *